United States Patent [19]

Apitz-Castro et al.

[11] Patent Number: 4,665,088

[45] Date of Patent: May 12, 1987

[54] (E-Z)-4,5,9-TRITHIADODECA-1,6,11-TRIENE 9-OXIDES

[75] Inventors: Rafael J. Apitz-Castro, Caracas, Venezuela; Mahendra K. Jain, Newark, Del.

[73] Assignee: The Research Foundation of State University of New York, Albany, N.Y.

[21] Appl. No.: 671,320

[22] Filed: Nov. 14, 1984

[51] Int. Cl.$^4$ ............................................. A61K 31/105
[52] U.S. Cl. ...................................... 514/420; 514/56; 514/164; 514/258; 514/457; 514/707; 514/469; 514/301; 568/22
[58] Field of Search .................. 568/22; 514/707, 420, 514/56, 164, 457, 258, 469, 301

[56] References Cited

U.S. PATENT DOCUMENTS

| | | | |
|---|---|---|---|
| 2,446,072 | 7/1948 | Armstrong | 260/608 |
| 2,508,745 | 5/1950 | Cavallito et al. | 260/453 |
| 2,554,088 | 6/1951 | Cavallito | 260/456 |
| 3,336,394 | 8/1967 | Lyness et al. | 260/607 |
| 3,428,665 | 2/1969 | Aichenegg et al. | 260/453 |
| 3,819,717 | 6/1974 | von Szczepanski et al. | 260/608 |

OTHER PUBLICATIONS

The Practice of Aromatherapy, Jean Valnet, Destiny Books, NYC, 1982, ISBN 0-89281-026-2, p. 131.
Thrombosis Research, 1983, vol. 32, No. 2, pp. 156-169.

*Primary Examiner*—Frederick E. Waddell
*Attorney, Agent, or Firm*—William J. Crossetta; Michael L. Dunn

[57] ABSTRACT

This invention relates to compounds of the structures:

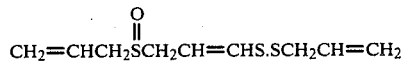

which structure includes its isomers, conventionally designated (E,Z)-4,5,9-trithiadodeca-1,6,11-triene 9-oxide and commonly termed (E,Z)-ajoene. This invention also relates to a process for preparing the compounds which comprises extracting and isolating allyl disulfide oxide (allyl 2-propenethiosulfinate) from the bulbs of garlic plants and thereafter treating it with a lower alkyl alcohol to produce such compound and the compounds as antibiotic and particularly as antithrombotic agents.

16 Claims, No Drawings

(E-Z)-4,5,9-TRITHIADODECA-1,6,11-TRIENE 9-OXIDES

FIELD OF THE INVENTION

This invention relates to new organic trithio oxides, their method of preparation from the common garlic and their use as antithrombotic agents.

DESCRIPTION OF THE PRIOR ART

The antibiotic activity of various sulfur containing organic compounds is known in the prior art. *Allium sativium*, the common garlic, has been known as having antibiotic and anticoagulant activity. U.S. Pat. Nos. 2,554,088 and 2,508,745 to Cavallito et al investigated various components of common garlic and disclosed thiosulfinates of the formula:

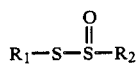

wherein $R_1$ and $R_2$ are alkyl, alkenyl, alicyclic or aromatic, as being active anti-bacterial and fungicidal agents. U.S. Pat. No. 3,336,394 discloses various unsaturated sulfides and sulfoxides of the formula:

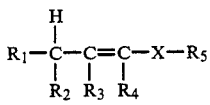

wherein $R_1$ and $R_5$ are alkyl (1-20 carbon atoms) or aryl (1-20 carbon atoms); $R_2$, $R_3$ and $R_4$ are hydrogen or alkyl (1-6 carbon atoms) and X is sulfur, sulfoxide, sulfone and thiosulfonate. These compounds are disclosed as surface active agents. U.S. Pat. No. 3,819,717 discloses asymmetrical tri- and tetra-sulfides as fungicidal and bactericidal compounds. U.S. Pat. No. 2,446,072 discloses alkyl sulfides which are said to have a garlic like odor and are useful as insecticides. U.S. Pat. No. 3,428,665 discloses acyl mono- and disulfides, useful as pesticides, defoliants and insecticides.

It is an object of this invention to provide new organic trithio oxides and a process for the preparation thereof.

Another object is to provide biologically active trithio oxides which are effective antibiotic substances.

A further object is to provide organic trithio oxides which are effective antithrombotic compounds.

SUMMARY OF THE INVENTION

This invention relates to compounds of the structure:

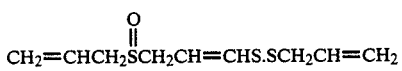

which structure includes its isomers, conventionally designated (E,Z)-4,5,9-trithiadodeca-1,6,11-triene 9-oxide and commonly termed (E,Z)-ajoene.

This invention also relates to a process for preparing the above-identified compounds which comprises extracting and isolating allyl disulfide oxide (allyl 2-propenethiosulfinate) from the bulbs of garlic plants and thereafter treating it with a lower alkyl alcohol to produce such compound.

A further aspect of this invention is the utility of the above-identified compounds as antibiotic and particularly as antithrombotic agents.

DETAILED DISCUSSION

Though it has long been theorized that various organic components found in common garlic may participate in its perceived activity as an anticoagulating agent, the compounds which have been extracted from garlic in the prior art have not shown a high level of anticoagulant activity in their pure form. We have discovered that when garlic is subjected to common extraction methods to obtain the allyl disulfide oxide product identified in U.S. Pat. No. 2,554,088 and the extraction product is then treated with a lower alkanoyl, that compounds never previously identified are formed which we have characterized as having the structure:

These compounds appear to be formed from the allyl disulfide oxide and have shown a higher degree of antithrombotic activity than previously identified in garlic extracts. Though we do not wish to be bound by the following, we theorize that the aforesaid compounds act to inhibit a membrane process which somehow involves the release reaction whereby autocoids are released from activated blood platelets which then stimulate the unactivated platelet population.

The preparation of the compounds of this invention of purity higher than 1% from the bulbs of the common garlic plant can be carried out through any convenient extraction procedure which acts to isolate the allyl disulfide oxide component of garlic so that such component can be thereafter dissolved in an appropriate lower alkanol for a time and at a temperature sufficient to form the compound of the instant invention. We have found that to obtain higher yields, the garlic portion should be freshly cut, chopped or ground. Whole garlic cloves reduce yield but can be satisfactorily used. The garlic pieces are then blended with a volatile, water-miscible organic solvent such as a lower alkanol, ether, or acetone and are allowed to sit for several hours or days. The particulate material is usually removed prior to further processing. We have found that vacuum concentration of the liquid and extraction of the aqueous residue with an appropriate solvent such as diethyl ether appears to increase the yield significantly. The extracted aqueous residue can be washed several times with water, dried and evaporated to increase the purity of the oil allyl disulfide oxide residue. The oily residue product is then dissolved in a volatile organic solvent such as acetone or a lower alkanol in mixture with water (10-90%) and maintained at a temperature of from about $-40°$ C. to a temperature less than about the reflux temperature of the organic solvent in mixture with water. Generally, the higher the temperature, the lower the amount of time the product must be maintained thereat. We have found that it is generally desirable to adjust temperature to achieve a maintenance time of several hours, usually from about 10-72 hours. The product, when subjected to chromatographic separation generally yields a mixture of (E,Z)-ajoene isomers.

Alternatively, a further method has been independently devised by Dr. Eric Block, which results in the synthetic manufacture of ajoene. Such method is not a portion of our invention herein claimed but as disclosed to us comprises the treatment of commercial allyl disulfide with an oxidizing agent to produce allyl 2-propenethiosulfinate and thereafter refluxing the allyl 2-propenethiosulfinate in an appropriate solvent, such as an acetone:water mixture to produce ajoene. Example I discloses the preparation of ajoene in this manner.

Though the compounds of this invention have multiple uses such as for example as bacteriocides and fungicides, a particularly important utility is as an antithrombotic agent. Various chemicals are known to cause blood platelets to aggregate which in turn can result in blood clots in the blood circulatory system of living systems. Certain other compounds are known to prevent blood platelet aggregation and accordingly are known herein as antithrombotic agents, while other compounds prevent clotting of aggregated platelets and are called anticoagulants. Both are used in the treatment of phlebitis, stroke, coronary thrombosis and arteriosclerosis. In a typical test to determine antithrombotic activity, the suspected antithrombotic chemical is mixed with a suspension of blood platelets, incubated for a few minutes, and then the suspension is treated with a known amount of a known agonist (agent inducing aggregation). The effectiveness of the suspected antithrombotic is compared to a control which has been treated with the agonist but which has not been treated with the antithrombotic and a quantitative measure of effectiveness is determined by ascertaining the concentration of suspected antithrombotic necessary to reduce by 50% the extent of platelet aggregation compared to the control. This measurement is termed the $ID_{50}$ of the antithrombotic. Typical agonists include collagen and ADP (adenosine diphosphate).

The instant (E,Z)-ajoene compounds have shown significant antithrombotic activity alone, in mixture with each other and particularly in combination with other known antithrombotics and anticoagulants. Mixtures of (E,Z)-ajoene with previously known antithrombotics and anticoagulants such as prostacyclin, indomethacin, aspirin, dipyridamole (Persantine), coumarin and its derivatives, heparin and ticlopidine can result in an aggragative effect potentiated up to 40 fold over that of previously known antithrombotics and anticoagulants.

The compounds of the instant claimed invention can be applied to mammals to achieve an antithrombotic effect by multiple diverse methods. Application can be direct to the blood circulatory system by intravenous, intraaterial or like paranteral means. Application can be indirect such as by intraperitoneal, subcutaneous or topical dermal application. We have found that intrapulmonary inhalation application, oral application and rectal application are also effective.

In instances where the preferred method of application is direct, effective dosage is in units of about 0.01 to about 100 mg/kg of body weight of the mammal, with no toxic side effects having manifested themselves in the extensive testing we have done. In instances where indirect application is preferred, we have found effective dosages to generally be from about 0.05 to about 200 mg/kg of body weight of the mammal. Generally then, the preferred range of application is from about 0.01 to about 200 mg/kg of body weight of the mammal. Repetition of dosage is of course dependent upon the specific subject but generally we have found that the antithrombotic effect remains for about 24 hours before a further dose is required.

We have found surprisingly, that combinations of the compounds of the instant invention with known antithrombotics and/or anticoagulants have the effect of potentiating antithrombotic and/or anticoagulant activity without any seeming harmful side effects. Indomethacin and prostacyclin show particularly enhanced antithrombotic activity when combined with the compounds of the instant claimed invention.

As with other pharmaceuticals, there is no unusual negative effect when mixing the compounds of the instant invention with various liquid or solid diluents or extenders appropriate for injection or encapsulating the compounds or mixtures used to form tablets or capsules. It is also considered part of this invention to add various stabilizing compounds to the (E,Z)-ajoene to increase shelf life, etc., under various environmental conditions.

The following representative examples have been provided to show preparation of the compounds of the invention and their antithrombotic utility:

EXAMPLE 1

Synthetic preparation of (E,Z)-4,5,9-trithiododeca-1,6,11-triene 9-oxide (ajoene)

Commercial diallyl disulfide was kept at a vacuum of 0.05 mm at 0° C. until all traces of diallyl sulfide have been removed, as indicated by gas chromatography. Peracetic acid (35%; 258 g, 1.187 mole) was added dropwise to a solution of disulfide (165 g, 1.13 mole) in chloroform (1800 ml) at 0° C. The reaction mixture was stirred at 0° C. for 30 minutes while anhydrous sodium carbonate (400 g) was added in small portions. The mixture was stirred for an additional 30 minutes at 0° C. and the filtered through a pad of Celite TM and anhydrous magnesium sulfate. The filtrate was concentrated under vacuum, ultimately using a vacuum of 0.05 mm for 1 hour to remove the last traces of acetic acid, and the product was determined to be crude allyl 2-propenethiosulfinate.

The crude allyl 2-propenethiosulfinate (154 g) from the above procedure was dissolved in a mixture of acetone and water (924 ml acetone, 616 ml water) and the homogeneous solution was heated at 50°–52° C. with stirring for 24 hours in a 2-liter round bottomed flask equipped with a reflux condenser. The reaction mixture was then diluted with methanol (2500 ml) and water 2500 ml) and extracted with hexane (20×500 ml). The aqueous-methanolic layer was saturated with ammonium sulfate and extracted with methylene chloride (5×500 ml). The methylene chloride layer was dried (magnesium sulfate) and concentrated in vacuum to give 53 g (34% yield) of (E,Z)-4,5,9-trithiadodeca-1,6,11-triene 9-oxide (ajoene), whose structure was established by proton and carbon-13 NMR, IR and chemical ionization mass spectrometry of the isomers separated by chromatography as well as spectroscopic properties of the mixture. The isomers could be easily separated by preparative HPLC (silica gel; 8:92 isopropanol:hexane). Elemental analysis: Calcd. for $C_9H_{14}S_3O$: C, 46.2; H, 5.98; S, 41.0. Found: C, 45.8; H, 5.90; S, 40.8.

EXAMPLE 2

Preparation of ajoene from garlic bulbs

Freshly chopped garlic bulbs (600 g) were soaked in methanol (3 L) for two days, the particulate matter was separated from the liquid, and the liquid was evaporated (50° C., under vacuum) to form a concentrate (100 ml). The concentrate was suspended in water (100 ml) and was extracted with diethyl ether (900 ml). The ether phase was washed several times with water, dried over anhydrous sodium sulphate and evaporated under vacuum. The resulting oily residue (3.2 gm) was dissolved in methanol (15 ml) and kept at $-20°$ C. for 4 days. The resulting solubilized product was separated from precipitated solids and mixed with 100 ml $H_2O$ and 100 ml of methanol. The mixture was extracted with pentane to facilitate subsequent chromatographic separation by removal of contaminants, and then extracted with methylene chloride to produce 0.589 grams of material. The material was subjected to silica gel chromatographic separation and eluted with ethyl acetate. Mixed (E,Z)-ajoene isomers (0.065 grams) were recovered and the isomers were subsequently separated by HPLC using a 9:1 mixture of hexane and isopropyl alcohol. The structures of the pure composition were identified and confirmed by proton and carbon-13 NMR, IR spectroscopy and chemical ionization mass spectrometry.

EXAMPLE 3

Platelet rich, citrated, human blood plasma (250,000 platelets/$\mu$L) was prepared and divided into 0.45 ml. aliquots for use in determining $ID_{50}$ levels of the subject compounds. The aliquots were treated with various quantities of (E)-ajoene, (Z)-ajoene, mixed (E,Z)-ajoene and mixed (E,Z)-ajoene together with prostacyclin and indomethacin. A control was maintained free of antithrombotic. The thus treated aliquots were pre-incubated by maintaining in an aggregometer cuvette for 2 minutes at 37° C. with stirring (950 RPM). Each aliquot was then further treated with an appropriate amount of ADP (10 $\mu$mole) or collagen (1 $\mu$g/ml or 2 $\mu$g/ml). Aggregation in each aliquot was monitored for a period of 3–5 minutes and percentage aggregation was quantitated by a dual channel aggregometer which ascertained percent aggregation by comparison against a control of light transmittance through the sample. The results can be found in the Table.

Generally, the prior art considers as $ID_{50}$ of less than 400$\mu$ moles in the above-identified tests as showing effective antithrombotic activity. Interestingly, a mixture of (E,Z)-ajoene isomers with prostacyclin or indomethacin appears to potentiate the $ID_{50}$ levels of both antithrombotic, an observation not previously reported.

TABLE

| Aliquot | Antithrombotic | ADP (10 $\mu$mole) | $ID_{50}$ ($\mu$mole) COLLAGEN (2 $\mu$g/ml) | COLLAGEN (1 $\mu$g/ml) |
|---|---|---|---|---|
| 1 | (Z)-ajoene | 188 ± 38 | 196 ± 64 | — |
| 2 | (E)-ajoene | 213 | 243 ± 90 | — |
| 3 | (E,Z)-ajoene 70:30 | — | — | 92.0 |
| 4 | Prostacyclin | — | — | 0.001 |
| 5 | (E,Z)-ajoene 70:30 | — | — | 2.3 |
|   | Prostacyclin | — | — | 0.001 |
| 6 | Indomethacin | — | — | 0.2 |
| 7 | (E,Z)-ajoene 70:30 | — | — | 4.5 |
|   | Indomethacin | — | — | 0.2 |

What is claimed is:

1. A compound of the formula:

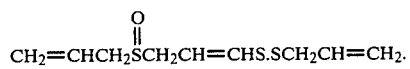

2. A method of preventing thrombosis of mammalian blood comprising applying to said blood an antithrombotic amount of a compound of the formula:

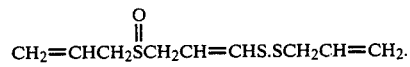

3. The method of claim 2 wherein said compound is applied in combination with another antithrombotic or anticoagulating compound.

4. The method of claim 3 wherein said other antithrombotic compound is selected from prostacyclin and indomethacin.

5. The method of claim 2 wherein said antithrombotic amount is from about 0.01 to about 200 mg of said compound per kilogram of body weight of the mammal.

6. A pharmaceutical preparation for preventing thrombosis of mammalian blood in a mammal comprising an effective amount of a compound of the formula:

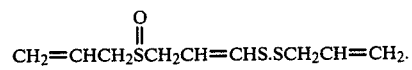

7. The pharmaceutical preparation of claim 6 in combination with another antithrombotic or anticoagulating compound.

8. The pharmaceutical preparation of claim 6 additionally containing a compound selected from prostacyclin and indomethacin.

9. The pharmaceutical preparation of claim 6 in combination with a liquid diluent.

10. The pharmaceutical preparation of claim 6 in combination with a solid extender.

11. The pharmaceutical preparation of claim 9 in combination with a stabilizer.

12. The pharmaceutical preparation of claim 10 in combination with a stabilizer.

13. A solid dosage unit for application to a mammal, for preventing thrombosis of mammalian blood, comprising an effective amount of the compound of claim 1 together with a carrier.

14. A method of potentiating the effect of a mammalian blood antithrombotic compound in a mammal comprising applying said antithrombotic compound to said mammalian blood in combination with an effective amount of a compound of the formula:

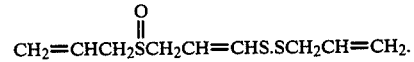

15. The method of claim 14 wherein said antithrombotic compound is selected from prostacyclin and indomethacin.

16. An antithrombotic composition comprising at least 1% of a compound of the formulation:

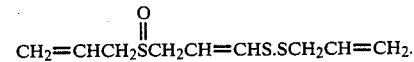

* * * * *